US012622705B2

(12) United States Patent
Xu

(10) Patent No.: US 12,622,705 B2
(45) Date of Patent: May 12, 2026

(54) ADAPTER OF CLIP APPLICATOR AND CLIP APPLICATOR

(71) Applicant: INTOCARE MEDICAL TECHNOLOGY (SUZHOU) CO., LTD., Suzhou (CN)

(72) Inventor: Ronghua Xu, Suzhou (CN)

(73) Assignee: INTOCARE MEDICAL TECHNOLOGY (SUZHOU) CO., LTD., Suzhou (CN)

( * ) Notice: Subject to any disclaimer, the term of this patent is extended or adjusted under 35 U.S.C. 154(b) by 556 days.

(21) Appl. No.: 18/245,394

(22) PCT Filed: Sep. 10, 2021

(86) PCT No.: PCT/CN2021/117631
§ 371 (c)(1),
(2) Date: Mar. 15, 2023

(87) PCT Pub. No.: WO2022/057733
PCT Pub. Date: Mar. 24, 2022

(65) Prior Publication Data
US 2023/0346388 A1 Nov. 2, 2023

(30) Foreign Application Priority Data

Sep. 18, 2020 (CN) .......................... 202010991628.8
Sep. 18, 2020 (CN) ........................ 202022057087.X
(Continued)

(51) Int. Cl.
*A61B 17/128* (2006.01)
*A61B 17/00* (2006.01)
(52) U.S. Cl.
CPC .... *A61B 17/128* (2013.01); *A61B 2017/0046* (2013.01)

(58) Field of Classification Search
CPC .............. A61B 17/128; A61B 17/1222; A61B 17/12009
See application file for complete search history.

(56) References Cited

U.S. PATENT DOCUMENTS 10,278,712 B2   5/2019   Edwards et al.
2003/0135224 A1*  7/2003   Blake, III .......... A61B 17/1285
606/143
(Continued)

FOREIGN PATENT DOCUMENTS

CN        106232273 A    12/2016
CN        111479521 A     7/2020
(Continued)

OTHER PUBLICATIONS

Extended European Search Report in EP 3 373 830 A0—mailed Jul. 10, 2024.

*Primary Examiner* — Martin T Ton
(74) *Attorney, Agent, or Firm* — McClure, Qualey & Rodack, LLP

(57) ABSTRACT

An adapter of a clip applicator and a clip applicator are provided. The adapter includes an adapter outer shell. The adapter outer shell includes an operation member capable of moving along a proximal-end direction and a distal-end direction: the adapter includes a lock mechanism, and the lock mechanism is arranged in the adapter outer shell; the operation member moves along the proximal-end direction under an action of an external force along the proximal-end direction, so that the lock mechanism allows a clip-cartridge assembly of the clip applicator to be plugged into the adapter outer shell and pulled out of the adapter outer shell; after the external force along the proximal-end direction disappears, the lock mechanism impels the operation member to move along the distal-end direction to an original position, and to
(Continued)

cooperate with a lock structure of the clip-cartridge assembly, so that the clip-cartridge assembly is locked in the adapter.

12 Claims, 7 Drawing Sheets

(30)     Foreign Application Priority Data

Oct. 15, 2020   (CN) ......................... 202011105224.0
Oct. 15, 2020   (CN) ......................... 202022298510.5

(56)     References Cited

U.S. PATENT DOCUMENTS

2017/0290587 A1* 10/2017 Schober ........... A61B 17/07207
2018/0317927 A1* 11/2018 Cai .................... A61B 17/1285
2019/0053808 A1*  2/2019 Baril ...................... A61B 90/08
2021/0059681 A1   3/2021 Zhang et al.
2021/0204956 A1*  7/2021 Thomas ............. A61B 17/1285

FOREIGN PATENT DOCUMENTS

CN          213156189 U      5/2021
WO          2017079895 A1    5/2017

* cited by examiner

111

11161

2

22

21

ADAPTER OF CLIP APPLICATOR AND CLIP APPLICATOR

The present application claims priorities of Chinese Patent Application No. 202010991628.8 and No. 202022057087.X filed on Sep. 18, 2020, and claims priorities of Chinese Patent Application No. 202011105224.0 and No. 202022298510.5 filed on Oct. 15, 2020, the contents of the above Chinese patent applications are incorporated herein by reference in their entirety as part of the present application.

TECHNICAL FIELD

The present disclosure relates to a field of medical instrument, and more particularly, to an adapter of a clip applicator and a clip applicator.

BACKGROUND

A surgical clip applicator is usually configured for clipping a tubular tissue during surgical operation, so as to avoid exudation of fluid of the tubular tissue.

In the prior art, a clip-cartridge assembly of the clip applicator is detachably mounted on an adapter of the clip applicator and is in signal communication with the adapter; the adapter identifies the information of clips in the clip-cartridge assembly so as to execute a corresponding program action. During assembling and disassembling the clip-cartridge assembly and the adapter, a structure of a connection portion between the adapter and the clip-cartridge assembly is complex, which is not convenient for assembling and disassembling the clip-cartridge assembly, and thus is not convenient for user's operation, rendering low operation efficiency.

SUMMARY

(I) Technical Problems to be Solved

In order to solve the above-described problems of the prior art, the present disclosure provides an adapter of a clip applicator and a clip applicator, which is convenient for assembling and disassembling (i.e. plug-in and pull-out) between the clip-cartridge assembly and the adapter, and has a fool-proof effect.

(II) Technical Solutions

In order to achieve the above-described purpose, a main technical solution adopted by the present disclosure includes:

On aspect of the present disclosure provides the adapter of the clip applicator; the adapter of the clip applicator includes an adapter outer shell; the adapter outer shell comprises an operation member capable of moving along a proximal-end direction and a distal-end direction; the adapter further comprises a lock mechanism, and the lock mechanism is arranged in the adapter outer shell; the operation member moves along the proximal-end direction under an action of an external force along the proximal-end direction, so that the lock mechanism allows a clip-cartridge assembly of the clip applicator to be plugged into the adapter outer shell and pulled out of the adapter outer shell; after the external force along the proximal-end direction disappears, the lock mechanism impels the operation member to move along the distal-end direction to an original position, and to cooperate with a lock structure of the clip-cartridge assembly, so that the clip-cartridge assembly is locked in the adapter.

Preferably, the adapter outer shell comprises a main body outer shell and a rotation outer shell, the rotation outer shell is rotatably connected to the main body outer shell; the rotation outer shell comprises a distal rotation shell and a proximal rotation shell that are separable from each other, the proximal rotation shell serves as the operation member, and an original position of the proximal rotation shell is a position where the proximal rotation shell is connected with the distal rotation shell; or the rotation outer shell is provided with an operation portion capable of moving along the proximal-end direction and the distal-end direction, and the operation portion serves as the operation member.

Preferably, the adapter of the clip applicator further comprises a guide ring, the guide ring extends from a proximal end of the rotation outer shell into the rotation outer shell, and the proximal end of the guide ring is connected with the main body outer shell; a guide portion is arranged on the guide ring and the rotation outer shell, and the guide portion provides a two-way automatic guide for the clip-cartridge assembly during a process that the clip-cartridge assembly is plugged into the rotation outer shell; the lock mechanism and the lock structure are matched on the basis of two-way automatic guide.

Preferably, the lock mechanism comprises a plug slot respectively arranged on distal ends of the guide ring and the rotation outer shell, and is configured to be connected with a plug member on the clip-cartridge assembly to provide a circumferential lock; the guide portion of the guide ring and the rotation outer shell are both arranged as a guide groove respectively at the distal ends of the guide ring and the rotation outer shell, and the guide groove extends from a position of a distal-end surface along a circumferential direction and gradually increases in depth during a process of extending to be connected with the plug slot.

Preferably, the lock mechanism further comprises a lock ring, a limit member, an elastic member and a lock member; the lock ring is adjacent to the proximal rotation shell/the operation portion and is slidably sleeved on the guide ring, the limit member is fixed on an outer side of the guide ring, the elastic member is sleeved on the outer side of the guide ring, and provides an axial limit to the lock ring together with the limit member; the lock member is arranged on the guide ring; when the lock ring is subjected to the external force of the proximal rotation shell/the operation portion along the proximal-end direction: the lock ring moves along the proximal-end direction and impels the lock member not to lock the clip-cartridge assembly, and the lock ring compresses the elastic member; after the external force acting on the lock ring disappears: the elastic member impels the lock ring to move along the distal-end direction and the lock ring pushes the proximal rotation shell/the operation portion to move along the distal-end direction until the lock ring abuts against the limit member, at this time, the proximal rotation shell is connected with the distal rotation shell/the operation portion is located at the original position, and the lock ring impels the lock member provides at least axial lock with a lock groove of the clip-cartridge assembly.

Preferably, one lock member is arranged along one circumference or at least two lock members are evenly arranged along one circumference, the guide ring is provided with an auxiliary lock structure configured for cooperating with an auxiliary lock mechanism in the clip-cartridge assembly, and the auxiliary lock mechanism and the auxiliary lock structure are matched on the basis of two-way automatic guide; or lock members are arranged along a plurality of circumferences, each circumference comprises one lock member or at least two lock members evenly arranged; the lock member is a lock bead, the guide ring is provided with a mounting hole for accommodating the lock bead, a diameter of the mounting hole at an inner wall of the guide ring is smaller than a diameter of the mounting hole at an outer wall of the guide ring, a diameter of the lock bead is between the diameter of the mounting hole at the inner wall of the guide ring and the diameter of the mounting hole at the outer wall of the guide ring, an inner surface of the lock ring comprises an abutting annular surface and an annular slope connected along the distal-end direction, and the annular slope is inclined outward along the distal-end direction; when the lock ring abuts against the limit member, an outer end of the lock bead abuts against the abutting annular surface; and the lock ring moves along the proximal-end direction, so that the lock bead disengages from the abutting annular surface, and the lock bead moves outward under an action of an outward external force.

The other aspect of the present disclosure provides a clip applicator, the clip applicator comprises a clip-cartridge assembly, and the clip applicator further comprises the adapter as described above; the clip-cartridge assembly is provided with a lock structure; when the operation member moves along the proximal-end direction under the action of the external force along the proximal-end direction, the clip-cartridge assembly is allowed to be plugged into the adapter outer shell and pulled out of the adapter outer shell; after the external force along the proximal-end direction disappears, the lock mechanism cooperates with the lock structure so that the clip-cartridge assembly is locked in the adapter outer shell.

Preferably, the clip-cartridge assembly comprises a lock structure and an auxiliary lock mechanism, the lock structure cooperates with the lock mechanism of the adapter, and the auxiliary lock mechanism cooperates with an auxiliary lock structure of the adapter, so that double locking is provided; the auxiliary lock mechanism and the auxiliary lock structure lock the clip-cartridge assembly in the adapter outer shell when the clip-cartridge assembly is plugged in place; and a process of the clip-cartridge assembly moving along the distal-end direction due to an external force along the distal-end direction impels the auxiliary lock mechanism and the auxiliary lock structure to disengage from each other.

Preferably, the clip-cartridge assembly comprises a clip-cartridge outer shell, the clip-cartridge outer shell comprises a clip-cartridge fixation shell and a clip-cartridge rotation shell that are rotatably connected with each other, an identification signal generation structure is arranged at a proximal end of the clip-cartridge fixation shell, an identification signal receiver is fixed in the adapter, and the identification signal receiver is in signal communication with the identification signal generation structure; the adapter outer shell comprises a main body outer shell and a rotation outer shell, and the rotation outer shell is rotatably connected to the main body outer shell; through cooperation of the lock mechanism and the lock structure, the clip-cartridge fixation shell and the guide ring are optionally locked, and the clip-cartridge rotation shell and the rotation shell are optionally locked; the auxiliary lock mechanism cooperates with the auxiliary lock structure on the guide ring to lock the clip-cartridge fixation shell and the guide ring when the clip-cartridge assembly is plugged in place.

Preferably, the auxiliary lock mechanism comprises an elastic ring located in an inner wall groove of the clip-cartridge fixation shell, and one or at least two positioning protrusions connected to the elastic ring; the auxiliary lock structure is one or at least two positioning holes arranged on an inner wall of the guide ring, and the positioning protrusion runs through a through hole on the clip-cartridge fixation shell to engage with the positioning hole.

Preferably, the lock structure comprises a lock groove arranged on an outer surface of the clip-cartridge fixation shell, and the lock groove is locked with the lock bead; the lock structure further comprises a plug member arranged on the clip-cartridge fixation shell, the plug member is plugged into a plug slot on the guide ring, and plug between the plug member and the plug slot provides a circumferential lock of the clip-cartridge fixation shell and the guide ring; the lock structure further comprises a plug member arranged on the clip-cartridge rotation shell, the plug member is plugged into a plug slot on the rotation outer shell, and plug between the plug member and the plug slot provides a circumferential lock of the clip-cartridge rotation shell and the rotation outer shell; an axial distance between the plug member on the clip-cartridge fixation shell and the plug member on the clip-cartridge rotation shell is greater than an axial distance between the plug slot on the guide ring and the plug slot on the rotation outer shell.

Preferably, the identification signal generation structure is an identification information storage chip, the identification information storage chip is provided with two groups of pin needles that are in signal communication with the identification signal receiver, and when the plug member is plugged into the plug slot, the identification signal receiver is connected with at least one group of pin needles; each group of pin needles comprises one or at least two pin needles.

(III) Advantageous Effects

Advantageous effects of the present disclosure are as follows:

The adapter of the clip applicator according to the present disclosure, by pulling the operation member of the adapter outer shell along the proximal-end direction, the lock mechanism does not limit plugging in and pulling out of the clip-cartridge assembly, at this time, the clip-cartridge assembly is plugged in and pulled out freely. After the clip-cartridge assembly is plugged into the adapter, the clip-cartridge assembly and the adapter are locked by canceling the pulling force along the proximal-end direction. Therefore, assembling and disassembling (i.e. plug in and pull out) of the clip-cartridge assembly is convenient, which is convenient for an operation of a user, and further improves the operation efficiency. Meanwhile, the clip-cartridge assembly is not capable of being plugged in and pulling out at a non-mounting position, which prevents the clip-cartridge assembly from being plugged in and pulled out by error to cause adverse consequences, and has a fool-proof effect, thereby improving safety and reliability.

The clip applicator provided by the present disclosure allows assembling and disassembling (i.e. plug in and pull out) of the clip-cartridge assembly convenient, which is convenient for an operation of a user, and further improves the operation efficiency. Meanwhile, the clip-cartridge assembly is not capable of being plugged in and pulling out at a non-mounting position, which prevents the clip-cartridge assembly from being plugged in and pulled out by error, and has a fool-proof effect.

REFERENCE SIGNS

1: clip-cartridge assembly; 11: clip-cartridge outer shell; 111: clip-cartridge fixation shell; 1111: first plug member; 1112: lock groove; 1113: positioning protrusion; 1114: elastic ring; 1115: clip-cartridge shaft; 1116: identification information storage chip; 11161: pin needle; 1117: mushroom-shaped tab; 1118: elastic seat; 112: clip-cartridge rotation shell; 1121: second plug member; 12: rod; 13: end effector; 2: adapter; 21: rotation outer shell; 211: distal rotation shell; 212: proximal rotation shell; 2121: lock ring; 21211: annular slope; 21212: abutting annular surface; 2122: limit member; 2123: elastic member; 2124: guide ring; 2125: lock member; 2126: positioning hole; 2127: first plug slot; 2128: first guide portion; 22: main body outer shell; 221: drive shaft.

DETAILED DESCRIPTION

In order to better explain the present disclosure and make it easier to be understood, the present disclosure will be described below in detail through specific embodiments in conjunction with the accompanying drawings. In the description of the present disclosure, the "distal" end refers to an end close to a patient, and the "proximal" end refers to as end close to an operator; in the description of the present disclosure, the "circumferential direction" refers to a direction perpendicular to an axis of the clip-cartridge assembly and the adapter.

Embodiment I

As shown in FIG. 1 to FIG. 9, this embodiment provides a clip applicator; and the clip applicator includes a clip-cartridge assembly 1 and an adapter 2.

Figure 1:
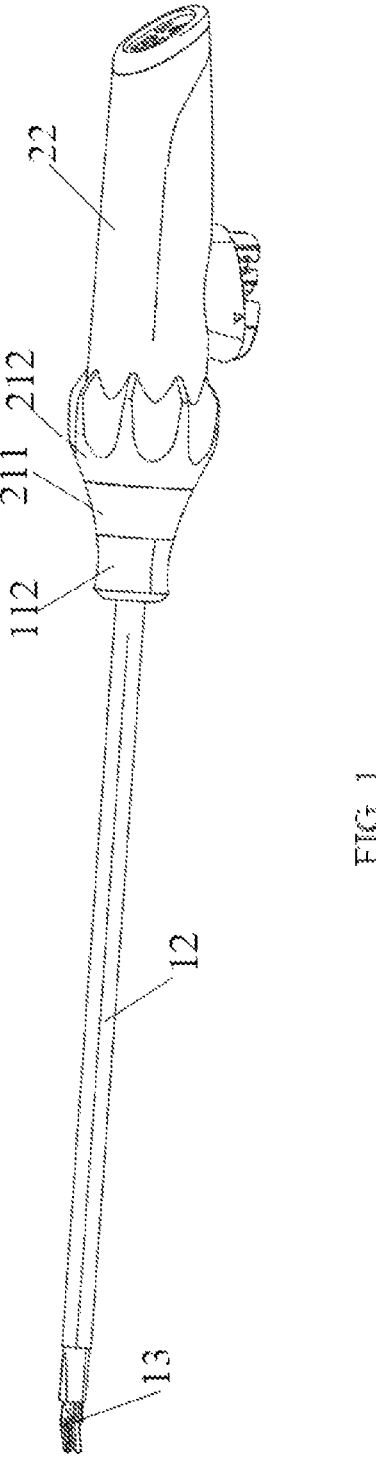
FIG. 1 is a structural schematic view of Embodiment 1 of a clip applicator provided by the present disclosure.
Figure 2:
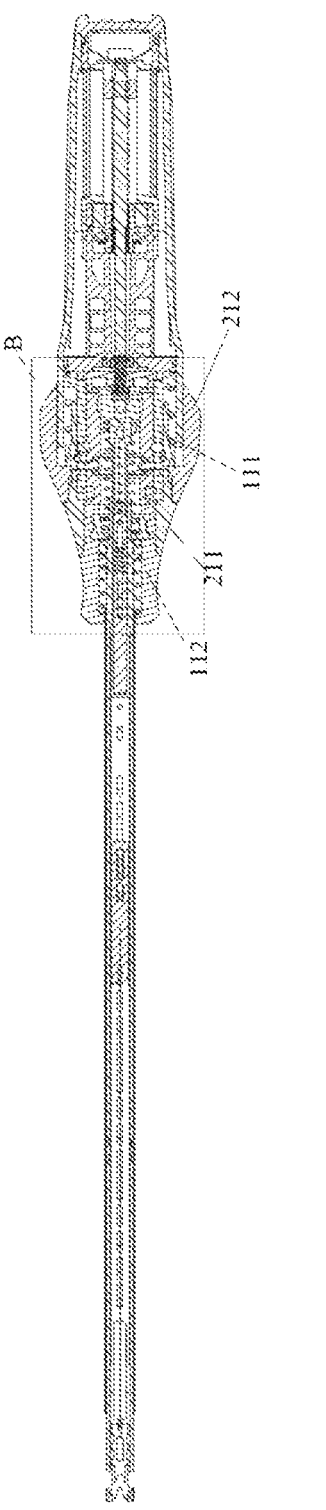
FIG. 2 is a cross-sectional schematic view of the clip applicator in FIG. 1.
Figure 5:
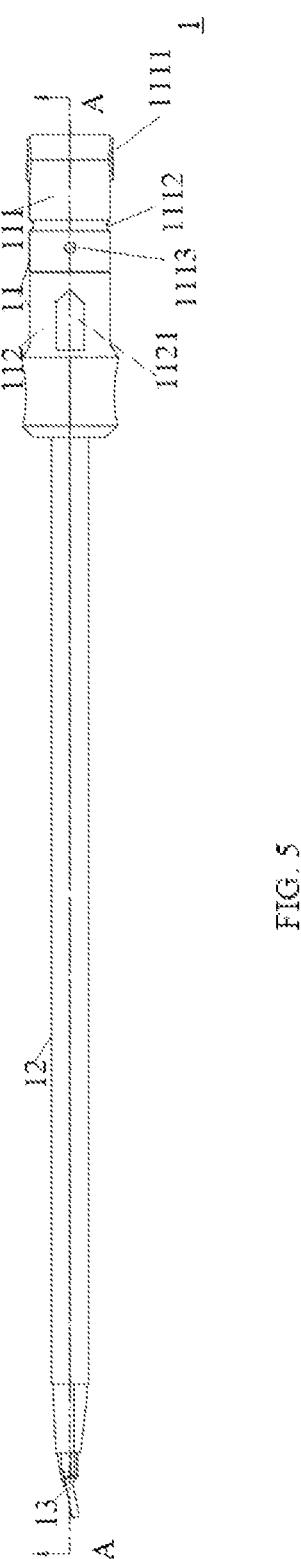
FIG. 5 is a structural schematic view of the clip-cartridge assembly in the clip applicator of FIG. 1.

As shown in FIG. 1 and FIG. 5, the clip-cartridge assembly 1 includes a clip-cartridge outer shell 11, a rod 12, and an end effector 13.

In this embodiment, the clip-cartridge outer shell 11 is provided to include two shells that are rotatable relative to each other. That is, the clip-cartridge outer shell 11 includes a clip-cartridge fixation shell 111 and a clip-cartridge rotation shell 112; the clip-cartridge rotation shell 112 is rotatably connected to a distal end of the clip-cartridge fixation shell 111; and a proximal end of the clip-cartridge fixation shell 111 is provided with an identification signal generation structure in signal communication with an identification signal receiver fixed in the adapter 2. The clip-cartridge fixation shell 111 and the clip-cartridge rotation shell 112 are provided therein with accommodation cavities that are communicated with each other. In this embodiment, the clip-cartridge fixation shell 111 and the clip-cartridge rotation shell 112 are both revolution bodies, and axes of the clip-cartridge fixation shell 111 and the clip-cartridge rotation shell 112 coincide with each other. Preferably, each of the clip-cartridge fixation shell 111 and the clip-cartridge rotation shell 112 is composed of two sub-shells that are symmetrically provided and spliced and fixed with each other by snapping, so as to facilitate assembling and disassembling of the clip-cartridge fixation shell 111 and the clip-cartridge rotation shell 112. It should be understood that a component in the clip-cartridge assembly 1 that needs to rotate during operation of the clip applicator is fixedly connected with the clip-cartridge rotation shell 112, and a component in the clip-cartridge assembly 1 that does not need to rotate during operation of the clip applicator is fixedly connected with the clip-cartridge fixation shell 111 (the "being fixedly connected" here is not defined as a non-detachable connection, but refers to a static connection relative to each other during operation).

As shown in FIG. 1, FIG. 2, FIG. 3, FIG. 4 and FIG. 8, the adapter 2 includes an adapter outer shell; the adapter outer shell includes a rotation outer shell 21 and a main body outer shell 22; the main body outer shell 22 is a portion that does not rotate during operation of the clip applicator; and the rotation outer shell 21 is rotatably connected to the main body outer shell 22, and is configured to drive a whole or a portion of the clip-cartridge assembly 1 to rotate. Preferably, the rotation outer shell 21 and the main body outer shell 22 are both revolution bodies, and axes of the rotation outer shell 21 and the main body outer shell 22 coincide.

Figure 3:
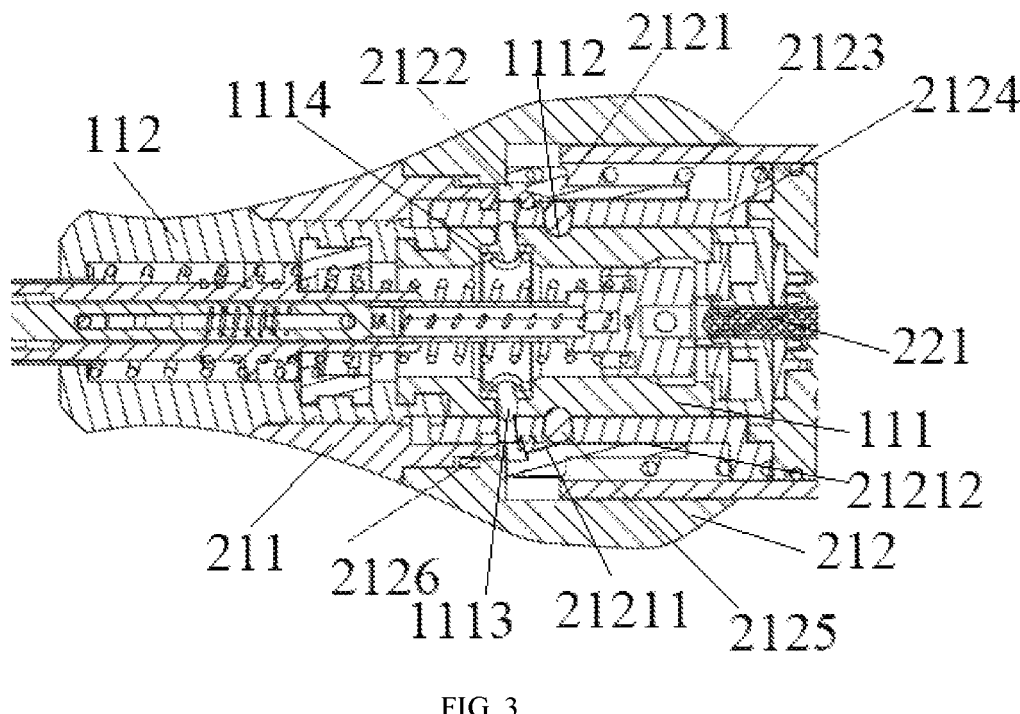
FIG. 3 is an enlarged view of portion B in FIG. 2, in which the adapter and the clip-cartridge assembly are locked.
Figure 4:
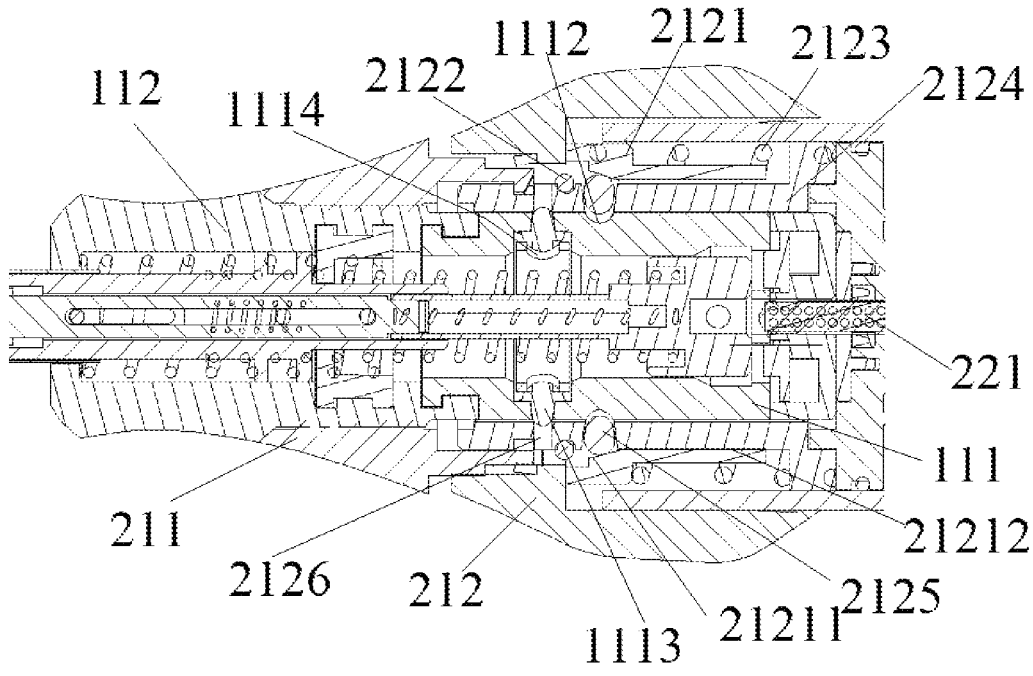
FIG. 4 is an enlarged view of another state of portion B in FIG. 2, in which the adapter and clip-cartridge assembly are unlocked.

As shown in FIG. 1 to FIG. 4 and FIG. 8, the rotation outer shell 21 includes a distal rotation shell 211 and a proximal rotation shell 212; and the distal rotation shell 211 and the proximal rotation shell 212 are separable from each other. In the case that the distal rotation shell 211 and the proximal rotation shell 212 are connected with each other, the proximal rotation shell 212 is located in a lock position (as shown in FIG. 3); the proximal rotation shell 212 moves along a proximal-end direction under an action of an external force along the proximal-end direction, so as to separate from the distal rotation shell 211, and then move on for another distance along the proximal-end direction to an unlock position (as shown in FIG. 4, that is, a fixed unlock position). The distal rotation shell 211 and the proximal rotation shell 212 are provided therein with cavities; the cavities of the distal rotation shell 211 and the proximal rotation shell 212 are communicated with each other to form an accommodation cavity of the rotation outer shell 21, and the accommodation cavity is configured to accommodate the clip-cartridge assembly 1, a lock mechanism (described in detail later) and some other components of the adapter. In this embodiment, each of the distal rotation shell 211 and the proximal rotation shell 212 is composed of two sub-shells that are symmetrically provided and spliced and fixed with each other by snapping, so as to facilitate assembling and disassembling of the distal rotation shell 211 and the proximal rotation shell 212. In addition, the distal rotation shell 211 and the proximal rotation shell 212 are both revolution bodies, and axes of the distal rotation shell 211 and the proximal rotation shell 212 coincide with each other.

Further, as shown in FIG. 1 to FIG. 4, a distal end of the proximal rotation shell 212 is connected with the distal rotation shell 211, and a proximal end of the proximal rotation shell 212 is sleeved on an outer side of a distal end of the main body outer shell 22. At least one group of mutual plug portions matching with each other is arranged at a connection joint between the distal rotation shell 211 and the proximal rotation shell 212; preferably, the connection between the distal rotation shell 211 and the proximal rotation shell 212 is achieved by tooth-shaped mutual plug portions, that is, a tooth of the distal rotation shell 211 is capable of plugging into a groove formed by two adjacent teeth of the proximal rotation shell 212, to implement circumferential fixation between the distal rotation shell 211 and the proximal rotation shell 212, so that the distal rotation shell 211 and the proximal rotation shell 212 are capable of rotating together when they are mutually plugged and they are separable from each other in an axial direction. For example, cylindrical teeth or end-surface teeth are selected. Arrangement of the tooth-shaped mutual plug portions achieves automatically aligning the distal rotation shell 211 with the proximal rotation shell 212.

In addition, an outer surface of the distal rotation shell 211 and an outer surface of the proximal rotation shell 212 are connected to form a smooth pear-shaped curved surface; and the outer surface of the proximal rotation shell 212 is protruding relative to the outer surface of the distal rotation shell 211. The above-described arrangement is convenient for an operator to hold. On the basis that the outer surface of the distal rotation shell 211 and the outer surface of the proximal rotation shell 212 are connected to form the smooth pear-shaped curved surface, the outer surface of the proximal rotation shell 212 for example is further provided thereon with a protruding protrusion to facilitate the operator to pull the proximal rotation shell 212 along the proximal-end direction.

Figure 6:
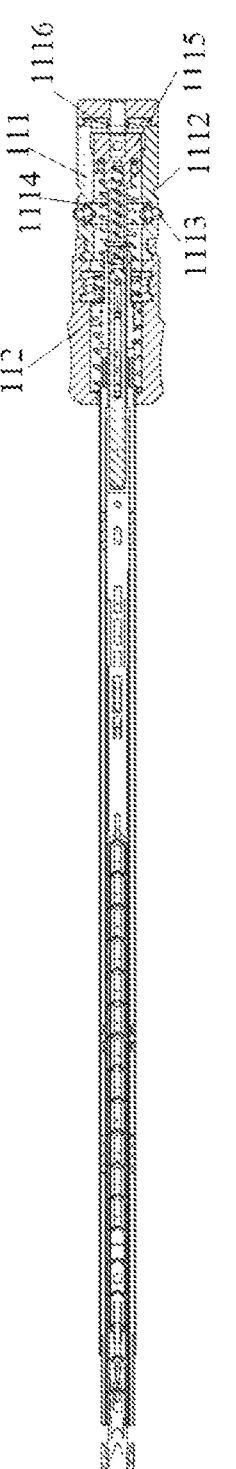
FIG. 6 is a cross-sectional schematic view taken along A-A line in FIG. 5.

As shown in FIG. 3 and FIG. 6, a portion of the clip-cartridge rotation shell 112 is inserted into the distal rotation shell 211; an exposed portion of the clip-cartridge rotation shell 112 is a visible outer shell; such visible outer shell of the clip-cartridge rotation shell 112 has an arc shape conforming to an ergonomic structure, to facilitate grasping and mounting of the clip-cartridge outer shell 11. Preferably, an edge of such visible outer shell of the clip-cartridge rotation shell 112 has an arc shape.

In this embodiment, the lock structure arranged in the clip-cartridge assembly 1 cooperates with the lock mechanism arranged in the rotation outer shell 21, to implement an optional circumferential lock between the clip-cartridge rotation shell 112 and the distal rotation shell 211, and implement an optional lock (including an axial lock and a circumferential lock) between the clip-cartridge fixation shell 111 and the main body outer shell 22. Because the clip-cartridge fixation shell 111 and the clip-cartridge rotation shell 112 are circumferentially rotatable relative to each other but are axially fixed, the axial lock between the main body outer shell 22 and the clip-cartridge fixation shell 111 also indirectly achieves an axial lock between the clip-cartridge rotation shell 112 and the main body outer shell 22.

With respect to the above-described arrangement, a size of the proximal rotation shell 212 is larger than a size of the distal rotation shell 211 for purpose of convenient grasping; so more sufficient space exists in the proximal rotation shell 212 to arrange the mechanism capable of implementing the axial lock; however, according to this embodiment, it is also easy for those skilled in the art to conceive of arranging the mechanism capable of implementing the axial lock in the distal rotation shell 211 and implementing the axial lock between the distal rotation shell 211 and the clip-cartridge rotation shell 112.

Specifically, the lock mechanism is correlated with the proximal rotation shell 212; the proximal rotation shell 212 moves from the lock position along the proximal-end direction to the unlock position under an action of an external force along the proximal-end direction, and meanwhile, the lock mechanism accumulates force; after the above-described external force along the proximal-end direction disappears, the accumulated force of the lock mechanism drives the proximal rotation shell 212 to move along the distal-end direction to the lock position. In the unlock position, the lock mechanism releases limit on a path of the clip-cartridge assembly 1 of the clip applicator entering and exiting the rotation outer shell 21, that is, the lock mechanism does not limits the entry and exit of the clip-cartridge assembly 1, and the clip-cartridge assembly 1 freely enter and exit the accommodation cavity of the rotation outer shell 21. In the lock position, the lock mechanism locks the clip-cartridge assembly 1 into the accommodation cavity of the rotation outer shell 21 (the clip-cartridge assembly 1 is not necessarily to be directly connected with the rotation outer shell 21), that is, the lock mechanism applies the circumferential lock and axial lock to the clip-cartridge assembly 1, and the clip-cartridge assembly 1 is incapable of being plugged in and pulled out; and meanwhile, the proximal rotation shell 212 is connected with the distal rotation shell 211, and the proximal rotation shell 212 and the distal rotation shell 211 are capable of rotating together. Therefore, the proximal rotation shell 212 moves along the proximal-end direction under the action of the external force along the proximal-end direction, so that the lock mechanism allows the clip-cartridge assembly 1 of the clip applicator to be plugged into the rotation outer shell 21 and pulled out of the rotation outer shell 21; after the above-described external force along the proximal-end direction disappears, the lock mechanism drives the proximal rotation shell 212 to move along the distal-end direction to be connected with the distal rotation shell 211, and the lock mechanism cooperates with the lock structure to lock the clip-cartridge assembly 1 in the adapter 2. When the clip-cartridge assembly 1 is locked in the adapter 2, the clip-cartridge assembly 1 rotates as driven by the adapter 2; in this case, the rotation of the clip-cartridge assembly 1 may be a rotation of an entirety of the clip-cartridge assembly 1, or may be a rotation of a portion of the clip-cartridge assembly 1 according to this embodiment, as long as an operation of the clip-cartridge assembly 1 is completed.

To sum up, because of the correlation between a portion (which is the proximal rotation shell according to this embodiment) of the rotation outer shell 21 and the lock mechanism, by pulling the portion of the rotation outer shell 21 along the proximal-end direction to the unlock position, the lock mechanism applies no limit on plugging-in and pulling-out of the clip-cartridge assembly 1, and at this time, the clip-cartridge assembly 1 is plugged in and pulled out freely; after the clip-cartridge assembly 1 is plugged into the adapter 2, the pulling force along the proximal-end direction is released so that the clip-cartridge assembly 1 and the adapter 2 are locked with each other. Therefore, the assembling and disassembling (i.e. plugging in and pulling out) of the clip-cartridge assembly 1 is convenient, which facilitates user's operation, and further improves operation efficiency. Meanwhile, the clip-cartridge assembly 1 is not capable of being plugged in and pulling out at a non-mounting position (i.e. at the lock position), which prevents the clip-cartridge assembly 1 from being plugged in and pulled out by error to cause adverse consequences, and has a fool-proof effect, thereby improving safety and reliability.

In this embodiment, as shown in FIG. 3, the adapter 2 further includes a guide ring 2124, the guide ring 2124 extends from the proximal end of the rotation outer shell 21 into the accommodation cavity of the rotation outer shell 21, and meanwhile is located in a proximal-end portion of the cavity of the distal rotation shell 211 and in the cavity of the proximal rotation shell 212; the guide ring 2124 is located in the interior of the distal end of the main body outer shell 21, and the proximal end of the guide ring 2124 is fixedly connected with the main body outer shell 22. Therefore, because the main body outer shell 22 is fixed during operation, the guide ring 2124 is also fixed during operation, that is, the rotation outer shell 22 is rotatable relative to the guide ring 2124. By arranging the guide ring 2124, on the one hand, the guide ring 2124 is configured for locking the clip-cartridge fixation shell 111 in the case that the clip-cartridge outer shell 11 of the clip-cartridge assembly 1 comprises the clip-cartridge fixation shell 111 and the clip-cartridge rotation shell 112, so that the clip-cartridge fixation shell 11 is indirectly and fixedly connected with the main body outer shell 22, thereby ensuring stability and reliability of signal transmission between the clip-cartridge fixation shell 11 and the main body outer shell 22; on the other hand, the guide ring 2124 is configured for automatically guiding the clip-cartridge assembly 1 during the process of plugging the clip-cartridge assembly 1 into the rotation outer shell 21, so that the lock mechanism is smoothly locked with the lock structure of the clip-cartridge assembly 1.

Figure 9:
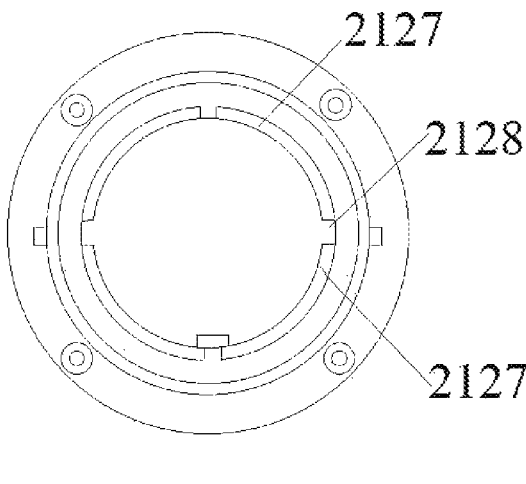
FIG. 9 is a structural schematic view of an end surface of a guide ring in the adapter.

First of all, referring to FIG. 5 and FIG. 9, the lock mechanism includes a first plug slot 2127 arranged at the distal end of the guide ring 2124 and a second plug slot arranged at the distal end of the distal rotation shell 211 (the arrangement of the second plug slot may refer to the arrangement of the first plug slot 2127); and each of the first plug slot and the second plug slot extends from the distal end toward the proximal end to form a groove. The lock structure includes a first plug member 1111 arranged at the proximal end of the clip-cartridge fixation shell 111 and a second plug member 1121 arranged at the proximal end of the clip-cartridge rotation shell 112. The first plug member 1111 is plugged into the first plug slot 2127, and the guide ring 2124 and the clip-cartridge fixation shell 111 achieve an optional circumferential lock with each other, that is, the guide ring 2124 and the clip-cartridge fixation shell 111 are incapable of rotating relative to each other. The second plug member 1121 is plugged into the second plug slot, and the distal rotation shell 211 and the clip-cartridge rotation shell 112 achieve an optional circumferential lock, that is, the distal rotation shell 211 and the clip-cartridge rotation shell 112 are incapable of rotating relative to each other.

In order to conveniently implement the plugging between the first plug slot 2127 and the first plug member 1111, as shown in FIG. 9, the guide ring 2124 is provided with a first guide portion 2128 for automatically guiding the clip-cartridge fixation shell 111 during the process that the clip-cartridge assembly 1 is plugged into the rotation outer shell 21; preferably, the clip-cartridge fixation shell 111 is plugged into the rotation outer shell 21 while the clip-cartridge fixation shell 111 rotates, so that the clip-cartridge fixation shell 111 is automatically guided.

Specifically, the first guide portion 2128 is a first guide groove arranged at the distal end of the guide ring 2124; and the first guide groove extends along a circumferential direction from a position of the distal-end surface of the guide ring 2124 and gradually increases in depth during the process of extending to be connected with the first plug slot 2127; so, as the clip-cartridge fixation shell 111 is plugged while rotating, the first guide groove guides the first plug member 1111, that needs to be plugged into the first plug slot 2127, of the clip-cartridge fixation shell 111 to the first plug slot 2127. In order that a rotary direction of the clip-cartridge fixation shell 111 during being plugged is not limited, two first guide grooves are symmetrically arranged on both sides of the first plug slot 2127, and the two first guide grooves gradually increase in depth as the two first guide grooves extend toward the first plug slot 2127 between them.

For example, a plurality of first plug slots 2127 are provided, in this case, the plurality of first plug slots 2127 are evenly arranged along the circumferential direction. A plurality of first guide portions 2128 are correspondingly arranged, and the plurality of first guide portions 2128 are arranged along the circumferential direction. Taking one first plug slot 2127 and two first guide portions 2128 on both sides of the one first plug slot 2127 as a group, respective groups are the same and are evenly arranged along the circumferential direction. Meanwhile, other structures of the lock mechanism are also evenly arranged along the circumferential direction, thereby making blind assembly possible, saving mounting procedures, and resulting an easy mounting. For example, the total number of first plug slots 2127 is one or at least two, and two first plug slots 2127 spaced apart from each other by 180° along the circumferential direction are preferred.

The plurality of first plug slots 2127 are evenly arranged along the circumferential direction, correspondingly, a plurality of first plug members 1111 are also evenly arranged along the circumferential direction. The first plug member 1111 of the clip-cartridge fixation shell 111 is a boss arranged on the outer surface of the clip-cartridge fixation shell 111; a proximal end of the boss gradually tapers to form a triangle, an arc or a trapezoid; and such design is favorable for smoothly and conveniently guiding the first plug member 1111. In this embodiment, the proximal end and the distal end of the boss are triangular, and a middle portion of the boss is rectangular, thereby the boss has a double-arrow-like shape. In this way, the tapering proximal end of the boss moves in the first guide groove with the rotation of the clip-cartridge assembly 1 until it reaches the first plug slot 2127 and is plugged into the first plug slot 2127. Because other structures (which will be explained in detail later, such as the lock member 2125, the lock groove 1112, the auxiliary lock mechanism, the auxiliary lock structure) that provide the circumferential lock between the clip-cartridge fixation shell 111 and the guide ring 2124 are provided, a size of the first plug member 1111 may be smaller.

Similarly, in order to conveniently implement plugging-in between the second plug slot and the second plug member 1121, the distal rotation shell 211 is provided with a second guide portion (which may be designed by referring to the first guide portion 2127) for automatically guiding the clip-cartridge rotation shell 112 during the process that the clip-cartridge assembly 1 is plugged into the rotation outer shell 21. Preferably, the clip-cartridge rotation shell 112 is automatically guided during the process of being plugged into the rotation outer shell 21 while rotating.

Specifically, the second guide portion is arranged at the distal end of the distal rotation shell 211, the second guide portion is a second guide groove, and the second guide groove extends along a circumferential direction from a position of the distal-end surface of the distal rotation shell 211 and gradually increases in depth during the process of extending to be connected with the second plug slot; so, as the clip-cartridge assembly 1 is plugged while rotating, the second guide groove guides the second plug member 1121, that needs to be plugged into the second plug slot, of the clip-cartridge assembly 1 to the second plug slot. In order that a rotary direction of the clip-cartridge rotation shell 112 during being plugged is not limited, two second guide grooves are symmetrically arranged on both sides of the second plug slot, and the two second guide grooves gradually increase in depth as the two second guide grooves extend toward the second plug slot between them.

For example, a plurality of second plug slots are provided, in this case, the plurality of second plug slots are evenly arranged along the circumferential direction. A plurality of second guide portions are correspondingly arranged, and the plurality of second guide portions are arranged along the circumferential direction. Taking one second plug slot and two second guide portions on both sides of the one second plug slot as a group, respective groups are the same and are evenly arranged along the circumferential direction. Meanwhile, other structures of the lock mechanism and communication devices are also evenly arranged along the circumferential direction, thereby making blind assembly possible, saving mounting procedures, and resulting an easy mounting.

The plurality of second plug slots are evenly arranged along the circumferential direction, correspondingly, a plurality of second plug members 1121 are also evenly arranged along the circumferential direction. The second plug member 1121 of the clip-cartridge rotation shell 112 is a boss arranged on the outer surface of the clip-cartridge rotation shell 112; a proximal end of the boss gradually tapers to form a triangle, an arc or a trapezoid; and such design is favorable for smoothly and conveniently guiding the second plug member 1121. In this embodiment, the proximal end of the boss is triangular, and the remaining portion of the boss is rectangular, thereby the boss has a single-arrow-like shape. In this way, the tapering proximal end of the boss moves in the second guide groove with the rotation of the clip-cartridge assembly 1 until it reaches the second plug slot and is plugged into the second plug slot.

By comparison, the reason why the first plug member 1111 has the double-arrow-like shape but the second plug member 1121 has the single-arrow-like shape is that: during the clip-cartridge assembly 1 is pulled out, an arrow at the distal end of the first plug member 1111 plays a role of guiding; and at this time, the clip-cartridge fixation shell and the clip-cartridge rotation shell are fixed relative to each other, so the first plug member 1111 simultaneously provides a guide for both the clip-cartridge fixation shell 111 and the clip-cartridge rotation shell 112 during the clip-cartridge assembly 1 is pulled out.

Because the boss serving as the first plug member 1111 and the boss serving as the second plug member 1121 are arranged on outer surfaces of the corresponding components, a radial size of the clip-cartridge rotation shell 112 is smaller than a radial size of the clip-cartridge fixation shell 111, so as to allow that the first plug member 1111 is plugged into the guide ring 2124 through the distal end of the rotation outer shell 21, or, the first plug member 1111 is plugged into the first plug slot through the second plug slot when the first plug slot and the second plug slot are aligned circumferentially.

Of course, the present disclosure is not limited thereto. The boss serving as the first plug member 1111 and the boss serving as the second plug member 1121 for example are provided to protrude from proximal-end surfaces of the corresponding components. However, no matter where the first plug member 1111 and the second plug member 1121 are provided, the first plug slot and the second plug slot may be bottomed or bottomless; when the first plug slot and the second plug slot are bottomed, the first plug member 1111 and the second plug member 1121 are regarded to get in place when they abut against the slot bottoms; and when the first plug slot and the second plug slot are bottomless, a special limit structure is arranged in the adapter.

In addition, the boss for example is a plug that is elastically connected with the clip-cartridge rotation shell 112 or the clip-cartridge fixation shell 111, and a deformation direction of the elastic connection is along an axial direction of the clip-cartridge rotation shell 112 or the clip-cartridge fixation shell 111, which, thus, prevents the plug slot from being missed due to fast rotation.

Because the clip-cartridge rotation shell 112 and the clip-cartridge fixation shell 111 are rotatable relative to each other, it is necessary to firstly hold and rotate the clip-cartridge fixation shell 111 to find an appropriate position. So an axial distance between the first plug member 1111 and the second plug member 1121 is greater than an axial distance between the first plug slot 2127 and the second plug slot.

As compared with the guide ring 2124 and the clip-cartridge fixation shell 111 that are further circumferentially locked through other structures, the distal rotation shell 211 and the clip-cartridge rotation shell 12 do not have any other circumferential lock structures than the second plug slot and the second plug member 1121; the second plug slot and the second plug member 1121 uniquely bear the optional circumferential lock function of the distal rotation shell 211 and the clip-cartridge rotation shell 12, so that the distal rotation shell 211 and the clip-cartridge rotation shell 112 are optionally locked together and rotate together without separation. Therefore, it should be clearly seen that a size of the second plug member 1121 is larger than a size of the first plug member 1111 to obtain a stable circumferential lock of the distal rotation shell 211 and the clip-cartridge rotation shell 12.

For example, in other embodiments, circumferential lock structures providing a main circumferential lock function are provided between the distal rotation shell 211 and the clip-cartridge rotation shell 112, and circumferential lock structures providing an auxiliary circumferential lock function are further provided for assisting the second plug slot and the second plug member 1121 (e.g., a positioning hole is provided on an inner wall of the distal rotation shell 211, and a positioning protrusion 1113 and an elastic ring 1114 are provided in the clip-cartridge rotation shell 112 of the clip-cartridge assembly 1, which may refer to similar structures arranged between the guide ring and the clip-cartridge fixation shell 111 described below).

In addition, it should be understood that if the size of the first plug member 1111 is large enough and actual conditions permit, cooperation between the first plug member 1111 and the first plug slot 2127 may replace one or two groups of the lock member 2125 and the lock groove 1112 (as described below) as well as the auxiliary lock mechanism and the auxiliary lock structure, to implement the optional lock between the guide ring and the clip-cartridge fixation shell 111.

Specifically, as shown in FIG. 3, the lock mechanism further includes a lock ring 2121, a limit member 2122, an elastic member 2123 and a lock member 2125. The lock structure further includes a lock groove 1112 arranged on the outer surface of the clip-cartridge fixation shell 111.

The lock ring 2121 is sleeved on the guide ring 2124; the lock ring 2121 is adjacent to the proximal rotation shell 212; and the lock ring 2121 and the proximal rotation shell 212 affect each other's movement along the proximal-distal direction, but do not rotate together (that is, when the proximal rotation shell 212 rotates, the lock ring 2121 does not rotate). The lock ring 2121 according to this embodiment is a revolution body formed by revolution of a Z-shaped plane, and an upper end of the Z shape of the lock ring 2121 is configured for be adjacent to the proximal rotation shell 212.

The limit member 2122 is fixed on an outer side of the guide ring 2124; in this embodiment, the limit member 2122 is an annular limit ring; an annular limit groove is provided on the outer circumferential wall of the guide ring 2124; the annular limit ring is arranged in the annular limit groove; and the annular limit ring is fixedly connected to the annular limit groove or is relatively tight plugged into the annular limit groove. The annular limit ring is capable of providing a stable and reliable blocking force, but the present disclosure is not limited thereto. For example, the limit member further includes one or more limit blocks; in the case that a plurality of limit blocks are provided; the plurality of limit blocks are arranged along the circumferential direction of the guide ring at intervals; and meanwhile, an annular limit groove or one or more independent limit grooves may be arranged on the guide ring to match with the limit blocks in a one-to-one manner.

In this embodiment, the elastic member 2123 is sleeved on the outer side of the guide ring 2124, and the limit member 2122 and the elastic member 2123 jointly constitute an axial limit to the lock ring 2121. In this embodiment, the elastic member 2123 is sleeved at the outer side of the proximal end of the lock ring; a bending at the outer surface of the Z-shaped lock ring forms a step; a distal end of the elastic member 2123 abuts against the step; and the proximal end of the elastic member 2123 is connected with a flange formed at the proximal end of the guide ring 2124. For example, in other embodiments, the elastic member 2123 is located at the proximal end of the lock ring, and the distal end of the elastic member 2123 abuts against the proximal end of the lock ring. A spring for example is selected as the elastic member 2123. In this embodiment, when deformation of the elastic member 2123 reaches maximum deformation, further movement of the lock ring is prevented, and the rotation outer shell 21 reaches the unlock position, and the lock mechanism is unlocked. Of course, the present disclosure is not limited thereto. The above-described unlock position for example is defined by arranging a limit structure in the adapter, for example, the distal end of the fixed main body outer shell of the adapter provides the limit structure, the rotation outer shell 21 is partially sleeved on the main body outer shell, an inner wall of the rotation outer shell 21 has a protrusion, and the rotation outer shell 21 is pulled toward the proximal end until the protrusion abuts against the distal end of the main body outer shell so as to reach the unlock position. The above-described arrangement of the unlock position implements functions of allowing plugging in and pulling out at a fixed unlock position and not allowing plugging in and pulling out at a position which is not the unlock position, so that misoperation is prevented.

The lock member 2125 is arranged on the guide ring 2124, and is configured for optional lock with the lock groove 1112 in the clip-cartridge assembly 1. In this embodiment, a plurality of lock members 2125 are evenly arranged along a circumferential direction. The lock member 2125 is a lock bead; the guide ring 2124 is provided thereon with a mounting hole for accommodating the lock bead; a diameter of the mounting hole at an inner wall of the guide ring 2124 is smaller than a diameter of the mounting hole at an outer wall of the guide ring; and a diameter of the lock bead is between the diameter of the mounting hole at the inner wall of the guide ring and the diameter of the mounting hole at the outer wall of the guide ring. The lock structure is a lock groove 1112 arranged on the clip-cartridge fixation shell 111. The lock structure for example includes a plurality of lock grooves 1112 (one lock groove 1112 corresponds to one lock bead or one lock groove 1112 corresponds to a plurality of lock beads), or the lock structure for example is an annular groove. Relatively, the annular groove has lower requirements for fabrication accuracy. In a case where a plurality of lock grooves 1112 cooperate with a plurality of lock beads, the circumferential lock and the axial lock are achieved; however, in a case where the lock structure is the annular groove, only the axial lock is achieved. In this embodiment, a plurality of lock grooves 1112 are evenly arranged along the circumferential direction of the clip-cartridge fixation shell 111, and preferably the plurality of lock grooves 1112 cooperate with the plurality of lock beads in one-to-one correspondence. When the first plug member 1111 and the second plug member 1121 are plugged in place, the lock bead corresponds to the lock groove 1112 in position. Moreover, because the plurality of lock grooves 1112 and the plurality of lock members 2125 are all evenly arranged, any lock member 2125 is capable of engaging with any lock groove 1112, which, in cooperation with the previous arrangement of plug and guide, makes blind assembly possible, allows mounting in both positive and negative directions, saves mounting procedures, and makes mounting easy.

The bent portion of the inner surface of the Z-shaped lock ring is a slope (referred to as an "annular slope 21211"); the annular slope 21211 is inclined outward along the distal-end direction; and the inner surface of the lock ring 2121 further includes an abutting annular surface 21212 connected to the proximal end of the annular slope 21211. When the lock ring 2121 abuts against the limit member 2122, an outer end of the lock bead abuts against the abutting annular surface 21212; at this time, if the clip-cartridge assembly 1 has been plugged into the rotation outer shell 22, the lock bead is plugged into the lock groove 1112. When the lock ring 2121 moves along the proximal-end direction until the lock bead disengages from the abutting annular surface 21212, the lock ring 2121 no longer limits the lock bead; if the lock bead is located at a lower half portion of the adapter 2 at this time, the lock bead moves out of the lock groove 1112 under gravity and disengages from the lock groove 1112; if the lock bead is located in a side portion or an upper half portion of the adapter 2 at this time, the lock bead still remains in the lock groove 1112, in this case, when the clip-cartridge assembly 1 is pulled out, a side wall of the lock groove 1112 applies a force on the lock bead, and the lock bead moves outward and finally disengages from the lock groove 1112. It should be understood that the above-described arrangement of the annular slope 21211 facilitates the outward movement of the lock bead.

Therefore, in this embodiment, the abutting annular surface 21212 of the lock ring 2121 presses the lock bead inward; when the clip-cartridge assembly 1 is plugged, the lock bead engages with the lock groove 1112 of the clip-cartridge assembly 1; when the clip-cartridge assembly 1 is not plugged, the lock bead does not falls out of the mounting hole because of the small diameter of the inner end of the mounting hole.

To sum up, when the lock ring 2121 abuts against the limit member 2122, the distal end of the lock ring 2121 abuts against the proximal rotation shell 212 so that the proximal rotation shell 212 is connected with the distal rotation shell 211, and the lock ring 2121 impels the lock member 2125 to lock (at least axially lock) the clip-cartridge assembly 1. When the lock ring 2121 moves with the proximal rotation shell 212 from the lock position along the proximal-end direction to the unlock position, the clastic member 2123 accumulates force and the lock ring 2121 allows the lock member 2125 to not lock the clip-cartridge assembly 1 (i.e., the lock member 2125 is capable of moving outward under an external force according to this embodiment). After the external force along the proximal-end direction disappears, the accumulated force of the elastic member 2123 impels the lock ring 2121 to drive the proximal rotation shell 212 to move along the distal-end direction to the lock position, and the lock ring 2121 impels the lock member 2125 to lock the clip-cartridge assembly 1. Therefore, when the lock ring 2121 is subjected to the external force of the proximal rotation shell 212 along the proximal-end direction, the lock ring 2121 moves along the proximal-end direction, so that the lock member 2125 does not lock the clip-cartridge assembly 1, and the lock ring 2121 compresses the elastic member 2123. After the external force applied on the lock ring 2121 disappears, the clastic member 2123 impels the lock ring 2121 to move along the distal-end direction and the lock ring 2121 pushes the proximal rotation shell 212 to move along the distal-end direction, until the lock ring 2121 abuts against the limit member 2122, at this time, the proximal rotation shell 212 is connected with the distal rotation shell 211, and the lock ring 2121 impels the lock member 2125 to at least axially lock with the lock groove 1112 of the clip-cartridge assembly 1.

The clip-cartridge assembly 1 further includes an auxiliary lock mechanism; the auxiliary lock mechanism is configured for cooperating the auxiliary lock structure on the guide ring 2124 to lock the clip-cartridge fixation shell 111 and the guide ring 2124 when the clip-cartridge assembly 1 is plugged in place. The process of the clip-cartridge assembly 1 moving along the distal-end direction due to the external force along the distal-end direction impels the auxiliary lock mechanism and the auxiliary lock structure to disengage from each other.

In this embodiment, the auxiliary lock mechanism includes an elastic ring 1114 and a plurality of positioning protrusions 1113 connected onto the clastic ring 1114; the elastic ring 1114 is located in an inner wall groove of the clip-cartridge fixation shell 111; an axis of the elastic ring 1114 coincides with an axis of the clip-cartridge fixation shell 111; the elastic ring 1114 does not disengage from the inner wall groove during use, but deforms in the inner wall groove. The auxiliary lock structure includes a plurality of positioning holes arranged on the inner wall of the guide ring 2124; and the plurality of positioning protrusions 1113 run through a plurality of through holes on the clip-cartridge fixation shell 111 in one-to-one correspondence to engage with the plurality of positioning holes in one-to-one correspondence. When the clip-cartridge assembly 1 is pulled outward, an outer end of the positioning protrusion 1113 is subjected to a force of an inner wall of the positioning hole provided on the guide ring 2124, and the positioning protrusion 1113 moves inward and drives the elastic ring 1114 to deform, until the positioning protrusion 1113 disengages from the positioning hole.

Preferably, the plurality of positioning protrusions 1113 are evenly arranged along the circumferential direction of the clastic ring 1114; and the plurality of positioning holes are evenly arranged along the circumferential direction of the guide ring; in this way, any positioning protrusion is capable of engaging with any positioning hole, which, in cooperation with the previous arrangement of plug, guide and the lock member 2125, makes blind assembly possible, allows mounting in both positive and negative directions, saves mounting procedures, and makes mounting easy. The total number of the positioning protrusion 1113 for example is one, which still implements the auxiliary lock; or the total number of the positioning protrusions 1113 for example is two or more, and the larger the total number is, the greater the locking strength is.

Therefore, the cooperation of the lock mechanism and the lock structure and the cooperation of the auxiliary lock mechanism and the auxiliary lock structure provide double locking, which makes connection between the adapter 2 and the clip-cartridge assembly 1 much firmer and improves locking safety. Of course, the double locking implemented in the present disclosure is not limited thereto; and instead of arrangement of the auxiliary lock structure and the auxiliary lock mechanism, lock members 2125 for example are arranged along a plurality of circumferences, and a plurality of lock members 2125 are evenly arranged along each circumference. For example, the lock members 2125 along different circumferences stagger from each other, so that a better lock effect is achieved; however, in this case, uniformity should be ensured when the plurality of lock members 2125 stagger from each other so that matching is easily implemented during blind assembly. Of course, the lock members 2125 along different circumferences may be arranged in a same way. The lock members 2125 are arranged along a plurality of circumferences, so that double locking or even more locking at different positions are implemented along the axis direction. When the lock member is the lock bead, for example, the inner surface of the lock ring is correspondingly provided with an annular slope.

In addition, the lock member 2125 for example is a positioning protrusion; the positioning protrusion is arranged in the mounting hole of the guide ring 2124 through a torsion spring. In addition, for example, the lock member 2125 is an elastic tongue.

Figure 7:
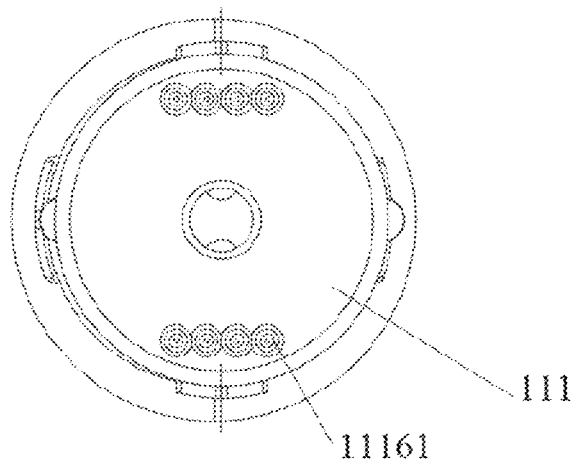
FIG. 7 is a structural schematic view of an end portion of a clip-cartridge fixation shell in FIG. 5.
Figure 8:
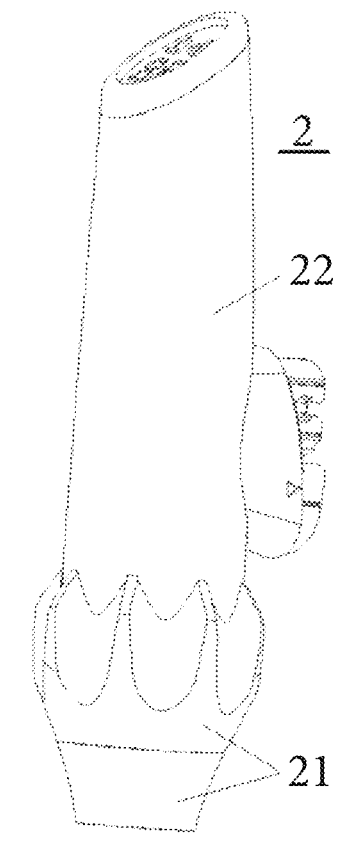
FIG. 8 is a structural schematic view of the adapter of the clip applicator in FIG. 1.

As shown in FIG. 6 to FIG. 7, in this embodiment, the identification signal generation structure is an identification information storage chip 1116; the identification information storage chip 1116 stores specification information of the clip-cartridge assembly 1, the specification information includes information of the clips in the clip-cartridge assembly 1. The identification information storage chip 1116 is provided with a plurality of groups of pin needles 11161 in signal communication with the identification signal receiver. When any group of the pin needles 11161 is in signal communication with the identification signal receiver, a signal communication is implemented, that is, it is not necessary that a designated pin needle 11161 is in signal communication with the identification signal receiver, which makes the signal communication between the clip-cartridge assembly 1 and the adapter 2 more convenient and allows mounting of the clip-cartridge assembly 1 in both positive and negative directions. When the plug member is plugged into the plug slot, there must be a group of pin needles 11161 connected with the identification signal receiver. As shown in FIG. 7, in this implementation, two groups of pin needles 11161 are provided, each group of pin needles 11161 includes 4 pin needles; however, each group of pin needles 11161 may include one or more pin needles, which is not limited. Preferably, a plurality of groups of pin needles

11161 are evenly arranged along the circumferential direction. In this embodiment, two groups of pin needles are spaced from each other by 180° along the circumferential direction. The double groups of pin needles according to this embodiment, in cooperation with the previous arrangement of plug, guide and the lock member, makes blind assembly possible, allows mounting in both positive and negative directions, saves mounting procedures, and makes mounting easy.

In general, the lock mechanism and the lock structure, the auxiliary lock mechanism and the lock structure, and the signal communication devices accurately match on the basis of two-way automatic guide, thereby making blind assembly possible.

Assembly steps of the clip-cartridge assembly 1 and the clip applicator according to this embodiment are described as follows:

S1: the operator pulls the proximal rotation shell 212 along the proximal-end direction to the unlock position; the proximal rotation shell 212 pushes the lock ring 2121 to move along the proximal-end direction, to compress the elastic member 223; and the annular slope 21211 of the lock ring 2121 moves to the outer side of the lock bead and does not limit the lock bead, so that the lock bead on the guide ring 2124 is in a free state;

S2: the clip-cartridge assembly 1 is plugged into the adapter 2 as a whole; when the first plug member 1111 abuts against the end portion of the guide ring 2124 during the plug process, the operator has an in-place feeling; the operator plugs the clip-cartridge fixation shell 111 along the proximal-end direction while rotating the clip-cartridge fixation shell 111; and the first guide groove guides the first plug member 1111 to enter the first plug slot 2127;

S3: the operator plugs the clip-cartridge rotation shell 112 along the proximal-end direction while rotating the clip-cartridge rotation shell 112; the second guide groove guides the second plug member 1121 to enter the second plug slot; in this process, the clip-cartridge rotation shell 112 pushes the clip-cartridge fixation shell 111 to continue to move in the first plug slot 2127 in a straight line along the proximal-end direction; and then the clip-cartridge rotation shell 112 is further pushed along the proximal-end direction until one of the first plug member 1111 and the second plug member is plugged in place. At this time, the lock bead already corresponds to the lock groove 1112 in position; the lock bead located at the upper half portion already falls into the lock groove 1112 due to gravity, and the positioning protrusion 1113 already bounces into the positioning hole, and the signal communication between the clip-cartridge assembly 1 and the adapter 2 is set up.

S4: the operator releases the proximal rotation shell 212; the elastic member 2123 pushes the lock ring 2121 to move toward the distal end until the lock ring 2121 abuts against the limit member 2122; movement of the lock ring 2121 toward the distal end drives the proximal rotation shell 212 to move toward the distal end and plugged and connected with the distal rotation shell 211; and the abutting annular surface 21212 of the lock ring 2121 pushes the lock bead to engage with the lock groove 1112. At this point, the clip-cartridge assembly 1 and the adapter 2 are locked together.

Disassembly steps of the clip-cartridge assembly 1 and the clip applicator according to this embodiment will be described as follows:

S1: the operator pulls the proximal rotation shell 212 along the proximal-end direction to the unlock position; the proximal rotation shell 212 pushes the lock ring 2121 to move along the proximal-end direction, to compress the elastic member 2123; and the annular slope 21211 of the lock ring 2121 moves to the outer side of the lock bead and does not limit the lock bead, so that the lock bead on the guide ring 2124 is in a free state, and the lock bead located at the lower half portion moves outward due to gravity and disengages from the lock groove 1112;

S2: the operator pulls out the clip-cartridge rotation shell 112 along the distal-end direction; the clip-cartridge rotation shell 112 drives the clip-cartridge fixation shell 111 to move toward the distal end; the outer wall of the clip-cartridge fixation shell 111 pushes the lock bead located at the upper half portion to disengage from the lock groove 1112; the outer wall of the guide ring 2124 pushes the positioning protrusion 1113 in the clip-cartridge fixation shell 111 that moves toward the distal end to move inward to disengage from the positioning hole. As the clip-cartridge assembly 1 moves along the distal-end direction as a whole, when the first plug member 1111 and the second plug member 1121 both disengage from their corresponding plug slots, the clip-cartridge assembly 1 is completely separated from the adapter 2.

When the clip applicator is operating, the clip-cartridge fixation shell 111 is fixed in the rotation outer shell 21 of the adapter 2 in a way that the clip-cartridge fixation shell 111 is static relative to the main body outer shell 22. The rod 12 of the clip-cartridge assembly 1 is partially fixed in the accommodation cavity of the clip-cartridge outer shell 11 along the axis of the rod 12 in a way of that the rod 12 rotates with the clip-cartridge rotation shell 112, and a clip to be applied is placed within the rod 12. One end (that is, a connecting end) of the end effector 13 of the clip-cartridge assembly 1 is connected with the rod 12; and in an actual operating process, the end effector 13 is a clamp for applying the clip.

In this embodiment, by arranging the clip-cartridge fixation shell 111 and the clip-cartridge rotation shell 112 that are rotatable relative to each other, the identification signal generation structure in the clip-cartridge fixation shell 111 is static relative to the main body outer shell 22 of the adapter 2 when the clip-cartridge assembly 1 is operating, which, thus, ensures reliability of signal transmission between the clip-cartridge assembly 1 and the adapter 2, and further ensures reliability of identification of the adapter 2.

In addition, the clip-cartridge assembly 1 includes a clip-cartridge shaft 1115; the main body outer shell 22 of the adapter 2 is provided with a drive shaft 221 that drives the clip-cartridge shaft 1115 to move; and the drive shaft 221 of the main body outer shell 22 is snapped with the clip-cartridge shaft 1115 of the clip-cartridge assembly 1, which further facilitates plugging in and pulling out of the clip-cartridge assembly 1.

In other embodiments of the present disclosure, the clip-cartridge outer shell 11 for example is a whole; in the case that the clip-cartridge outer shell 11 is a whole, the solution is changed into that the clip-cartridge outer shell 11 is locked with the guide ring 2124 and the guide ring 2124 is rotatably connected with the main body outer shell 22; and either the first plug slot 2127 and the first plug member 1111 as well as the corresponding guide portion, or the second plug slot, the second plug member 1121 as well as the corresponding guide portion as described above is reserved.

In other embodiments of the present disclosure, the rotation outer shell 21 for example are not designed as split bodies, but an operation portion (e.g., a pull block) capable of moving along the proximal-end direction and the distal-end direction is arranged on the rotation outer shell 21 to replace the proximal rotation shell 212. In this case, the lock mechanism is arranged in the rotation outer shell 21, the operation portion moves along the proximal-end direction under an action of an external force along the proximal-end direction, so that the lock mechanism allows the clip-cartridge assembly 1 of the clip applicator to be plugged into the rotation outer shell 21 and pulled out of the rotation outer shell 21. After the external force along the proximal-end direction disappears, the lock mechanism impels the operation portion to move along the distal-end direction to the original lock position, and to cooperate with the lock structure on the clip-cartridge assembly 1, so that the clip-cartridge assembly 1 is locked in the rotation outer shell 21. Specifically, when the lock ring 2121 is subjected to an external force of the operation portion along the proximal-end direction: the lock ring 2121 moves along the proximal-end direction, impels the lock member 2125 not to lock the clip-cartridge assembly, and the lock ring 2121 compresses the elastic member 2123; after the external force acting on the lock ring 2121 disappears: the elastic member 2123 impels the lock ring 2121 to move along the distal-end direction, and the lock ring 2121 pushes the operation portion to move along the distal-end direction until the lock ring 2121 abuts against the limit member 2122, at this time, the operation portion is located in the original lock position, and the lock ring 2121 impels the lock member 2125 to axially lock with the lock structure of the clip-cartridge assembly 1. In this case, the operation portion is adopted, the lock ring 2121 for example is changed into a non-annular lock member.

In addition, in other embodiments, the limit member 2122 for example is omitted; and in this case, just upon the accumulated force of the elastic member 2123 being exhausted, the lock ring 2121 just pushes the proximal rotation shell 212 to be connected with the distal rotation shell 211 or the lock ring 2121 just pushes the operation portion to the original position.

To sum up, the above embodiments take the case where each of the clip-cartridge outer shell and the adapter outer shell is split into two portions that are rotatable relative to each other as an example, but the present disclosure is also applicable without splitting the clip-cartridge outer shell and the adapter outer shell into two portions that are rotatable relative to each other. In this case, an operation member capable of moving along the proximal-end direction and the distal-end direction is directly arranged on the adapter outer shell (which for example is a rotatable portion of the adapter outer shell or a small operation portion). In this case, the operation member moves along the proximal-end direction under an action of an external force along the proximal-end direction, so that the lock mechanism allows the clip-cartridge assembly 1 of the clip applicator to be plugged into adapter outer shell and pulled out of the adapter outer shell; after the external force along the proximal-end direction disappears, the lock mechanism impels the operation member to move along the distal-end direction to the original lock position, and to cooperate with the lock structure on the clip-cartridge assembly 1, so that the clip-cartridge assembly 1 is locked in the adapter 2. In this case, all the above-described components linked with the rotation shell, the proximal rotation shell and the operation portion as well as corresponding relationships may be transferred to the operation member. Brief description will be given below, and corresponding parts of the above embodiments may be referred to for those not described specifically.

Preferably, the guide ring 2124 is arranged at the proximal end of the adapter outer shell; the guide portion is arranged on one or both of the guide ring 2124 and the adapter outer shell; the guide portion provides two-way automatic guide for the clip-cartridge assembly 1 during a process that the clip-cartridge assembly 1 is plugged into the adapter outer shell. The lock mechanism and the lock structure are matched on the basis of two-direction automatic guide.

Preferably, the lock mechanism includes the plug slots arranged at the distal ends of the guide ring 2124 and the adapter outer shell, and are configured for being connected with the plug members on the clip-cartridge assembly 1 to provide the circumferential lock. The guide portions of the guide ring 2124 and the rotation outer shell 21 are both arranged as the guide grooves at the distal ends of the guide ring 2124 and the rotation outer shell 21; and the guide groove extends from a position of the distal-end surface along a circumferential direction and gradually increases in depth during the process of extending to be connected with the plug slot.

Preferably, the lock mechanism further includes the lock ring 2121, the limit member 2122, the elastic member 2123 and the lock member 2125. The lock ring 2121 is adjacent to the operation member and is slidably sleeved on the guide ring 2124; the limit member 2122 is fixed on the outer side of the guide ring 2124; and the elastic member 2123 is sleeved on the outer side of the guide ring 2124, and provides the axial limit to the lock ring 2121 together with the limit member 2122.

The lock member 2125 is arranged on the guide ring 2124; when the lock ring 2121 is subjected to an external force of the operation member along the proximal-end direction: the lock ring 2121 moves along the proximal-end direction and impels the lock member 2125 not to lock the clip-cartridge assembly, and the lock ring 2121 compresses the elastic member 2123.

After the external force acting on the lock ring 2121 disappears: the elastic member 2123 impels the lock ring 2121 to move along the distal-end direction, and the lock ring 2121 pushes the operation member to move along the distal-end direction until the lock ring 2121 abuts against the limit member 2122, at this time, the operation member is located at the original position, and the lock ring 2121 impels the lock member 2125 to axially lock with the lock groove 1112 of the clip-cartridge assembly 1.

The clip-cartridge assembly 1 includes the clip-cartridge outer shell 11; the identification signal generation structure is arranged at the proximal end of the clip-cartridge outer shell 11; the identification signal receiver is fixed in the adapter 2; and the identification signal receiver is in signal communication with the identification signal generation structure. Through cooperation of the lock mechanism and the lock structure, the clip-cartridge outer shell 11 are optionally locked with the guide ring or the adapter outer shell.

The clip-cartridge assembly further includes an auxiliary lock mechanism; the auxiliary lock mechanism is configured for cooperating with the auxiliary lock structure on the guide ring 2124 and/or the adapter outer shell to lock the clip-cartridge outer shell 11 with the guide ring 2124 and/or the adapter outer shell when the clip-cartridge assembly is plugged in place. The movement of the clip-cartridge assembly 1 along the distal-end direction due to the action of the external force along the distal-end direction impels the auxiliary lock mechanism and the auxiliary lock structure to disengage from each other.

The auxiliary lock mechanism includes the elastic ring 1114 located in the inner wall groove of the clip-cartridge outer shell 11, and a plurality of positioning protrusions 1113 connected onto the elastic ring 1114. The auxiliary lock structure includes a plurality of positioning holes 2126 arranged on the inner wall of the guide ring 2124 and/or the adapter outer shell, and the positioning protrusion 1113 runs through the through hole on the clip-cartridge outer shell 11 to engage with the positioning hole 2126.

The lock structure includes the lock groove 1112 arranged on the outer surface of the clip-cartridge outer shell 11; and the lock groove 1112 is capable of being locked with the lock bead. The lock structure further includes the plug member arranged on the clip-cartridge outer shell 11; the plug member is capable of being plugged into the plug slot on the guide ring 2124 and/or the adapter outer shell; and the plugging of the plug member and the plug slot provides the circumferential lock between the clip-cartridge outer shell 11 and the guide ring 2124 and/or the adapter outer shell.

Further, each of the adapter outer shell and the clip-cartridge outer shell according to this embodiment is plastic or metal member formed by injection molding.

Embodiment 2

Figure 10:
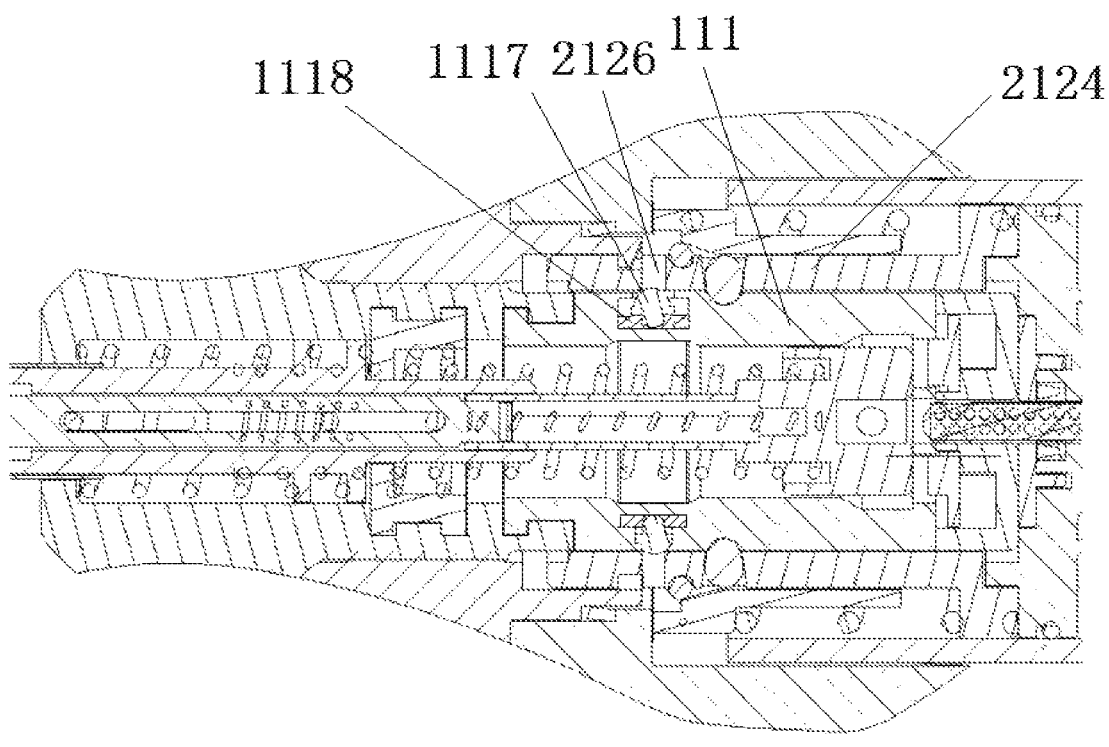
FIG. 10 is a partial cross-sectional schematic view of Embodiment 2 of the clip applicator provided by the present disclosure.

Referring to FIG. 10, a difference between this embodiment and Embodiment 1 is that the auxiliary lock mechanism is different. Specifically, in this embodiment, the auxiliary lock mechanism includes at least one group of a mushroom-shaped tab 1117 and an elastic seat 1118; an inverted trapezoidal groove comprising a wide hole located on an inner side and a narrow hole located on an outer side is arranged on the clip-cartridge fixation shell 111; the elastic seat 1118 is fixed in the wide hole; the elastic seat 1118 is a connection member that provides elasticity, such as a spring, a rubber pad, etc.; the mushroom-shaped tab 1117 includes a hemispherical head portion and a support portion located on an inner side of the hemispherical head portion; the support portion is connected between the hemispherical head portion and the elastic seat 1118; in a lock state, the hemispherical head portion of the mushroom-shaped tab 1117 runs through the narrow hole and enters the positioning hole 2126, to provide the auxiliary lock. During the clip-cartridge assembly is plugged in and pulled out, the hemispherical head portion of the mushroom-shaped tab 1117 disengages from the positioning hole 2126 due to abutting pressure of the inner wall of the guide ring 2124, and compresses the elastic pad 1118.

Preferably, a plurality of groups of the mushroom-shaped tab 1117 and the elastic seat 1118 are arranged; the plurality of mushroom-shaped tabs 1117 are evenly arranged along the circumferential direction of the clip-cartridge fixation shell 111, and the plurality of positioning holes are evenly arranged along the circumferential direction of the guide ring, so that any mushroom-shaped tab 1117 is capable of engaging with any positioning hole, which, in cooperation with the arrangement of plug, guide and the lock member as already described in detail in Embodiment 1, makes blind assembly possible, allows mounting in both positive and negative directions, saves mounting procedures, and makes mounting easy. It should be understood that the total number of the mushroom-shaped tab 1117 for example is one, which still implements the auxiliary lock; or the total number of the mushroom-shaped tabs 1117 for example is two or more; and the larger the total number is, the greater the locking strength is.

Although the embodiments of the present disclosure have been shown and described above, it should be understood that the above-described embodiments are exemplary and cannot be understood as limitations of the present disclosure; those ordinarily skilled in the art may make changes, modifications, replacements and variations to the above-described embodiments within the scope of the present disclosure.

The invention claimed is:

1. An adapter of a clip applicator, comprising an adapter outer shell, wherein
   the adapter outer shell comprises an operation member capable of moving along a proximal-end direction and a distal-end direction;
   the adapter further comprises a lock mechanism, and the lock mechanism is arranged in the adapter outer shell;
   the operation member moves along the proximal-end direction under an action of an external force along the proximal-end direction, so that the lock mechanism allows a clip-cartridge assembly of the clip applicator to be plugged into the adapter outer shell and pulled out of the adapter outer shell;
   after the external force along the proximal-end direction disappears, the lock mechanism impels the operation member to move along the distal-end direction to an original position, and to cooperate with a lock structure of the clip-cartridge assembly, so that the clip-cartridge assembly is locked in the adapter;
   the adapter outer shell comprises a main body outer shell and a rotation outer shell, the rotation outer shell is rotatably connected to the main body outer shell;
   the rotation outer shell comprises a distal rotation shell and a proximal rotation shell that are separable from each other, the proximal rotation shell serves as the operation member, and an original position of the proximal rotation shell is a position where the proximal rotation shell is connected with the distal rotation shell.

2. The adapter of the clip applicator according to claim 1, further comprising a guide ring, wherein
   the guide ring extends from a proximal end of the rotation outer shell into the rotation outer shell, and the proximal end of the guide ring is connected with the main body outer shell;
   a guide portion is arranged on the guide ring and the rotation outer shell, and the guide portion provides a two-way automatic guide for the clip-cartridge assembly during a process that the clip-cartridge assembly is plugged into the rotation outer shell;
   the lock mechanism and the lock structure are matched on the basis of two-way automatic guide.

3. The adapter of the clip applicator according to claim 2, wherein
   the lock mechanism comprises a plug slot respectively arranged on distal ends of the guide ring and the rotation outer shell, and is configured to be connected with a plug member on the clip-cartridge assembly to provide a circumferential lock;
   the guide portion of the guide ring and the rotation outer shell are both arranged as a guide groove respectively at the distal ends of the guide ring and the rotation outer shell, and the guide groove extends from a position of a distal-end surface along a circumferential direction and gradually increases in depth during a process of extending to be connected with the plug slot.

4. The adapter of the clip applicator according to claim 3, wherein the lock mechanism further comprises a lock ring, a limit member, an elastic member and a lock member;

the lock ring is adjacent to the proximal rotation shell and is slidably sleeved on the guide ring, the limit member is fixed on an outer side of the guide ring, the elastic member is sleeved on the outer side of the guide ring, and provides an axial limit to the lock ring together with the limit member;

the lock member is arranged on the guide ring;

when the lock ring is subjected to the external force of the proximal rotation shell along the proximal-end direction: the lock ring moves along the proximal-end direction and impels the lock member not to lock the clip-cartridge assembly, and the lock ring compresses the elastic member;

after the external force acting on the lock ring disappears: the elastic member impels the lock ring to move along the distal-end direction and the lock ring pushes the proximal rotation shell to move along the distal-end direction until the lock ring abuts against the limit member, at this time, the proximal rotation shell is connected with the distal rotation shell, and the lock ring impels the lock member provides at least axial lock with a lock groove of the clip-cartridge assembly.

5. The adapter of the clip applicator according to claim 4, wherein one said lock member is arranged along one circumference or at least two said lock members are evenly arranged along one circumference, the guide ring is provided with an auxiliary lock structure configured for cooperating with an auxiliary lock mechanism in the clip-cartridge assembly, and the auxiliary lock mechanism and the auxiliary lock structure are matched on the basis of two-way automatic guide;

the lock member is a lock bead, the guide ring is provided with a mounting hole for accommodating the lock bead, a diameter of the mounting hole at an inner wall of the guide ring is smaller than a diameter of the mounting hole at an outer wall of the guide ring, a diameter of the lock bead is between the diameter of the mounting hole at the inner wall of the guide ring and the diameter of the mounting hole at the outer wall of the guide ring, an inner surface of the lock ring comprises an abutting annular surface and an annular slope connected along the distal-end direction, and the annular slope is inclined outward along the distal-end direction;

when the lock ring abuts against the limit member, an outer end of the lock bead abuts against the abutting annular surface; and the lock ring moves along the proximal-end direction, so that the lock bead disengages from the abutting annular surface, and the lock bead moves outward under an action of an outward external force.

6. The adapter of the clip applicator according to claim 4, wherein the lock members are arranged along a plurality of circumferences, each circumference comprises one said lock member or at least two said lock members evenly arranged;

the lock member is a lock bead, the guide ring is provided with a mounting hole for accommodating the lock bead, a diameter of the mounting hole at an inner wall of the guide ring is smaller than a diameter of the mounting hole at an outer wall of the guide ring, a diameter of the lock bead is between the diameter of the mounting hole at the inner wall of the guide ring and the diameter of the mounting hole at the outer wall of the guide ring, an inner surface of the lock ring comprises an abutting annular surface and an annular slope connected along the distal-end direction, and the annular slope is inclined outward along the distal-end direction;

when the lock ring abuts against the limit member, an outer end of the lock bead abuts against the abutting annular surface; and the lock ring moves along the proximal-end direction, so that the lock bead disengages from the abutting annular surface, and the lock bead moves outward under an action of an outward external force.

7. A clip applicator, comprising a clip-cartridge assembly, wherein the clip applicator further comprises the adapter according to claim 1;

the clip-cartridge assembly is provided with the lock structure;

when the operation member moves along the proximal-end direction under the action of the external force along the proximal-end direction, the clip-cartridge assembly is allowed to be plugged into the adapter outer shell and pulled out of the adapter outer shell;

after the external force along the proximal-end direction disappears, the lock mechanism cooperates with the lock structure so that the clip-cartridge assembly is locked in the adapter outer shell.

8. The clip applicator according to claim 7, wherein the clip-cartridge assembly further comprises an auxiliary lock mechanism, and the auxiliary lock mechanism cooperates with an auxiliary lock structure of the adapter, so that double locking is provided;

the auxiliary lock mechanism and the auxiliary lock structure lock the clip-cartridge assembly in the adapter outer shell when the clip-cartridge assembly is plugged in place; and a process of the clip-cartridge assembly moving along the distal-end direction due to an external force along the distal-end direction impels the auxiliary lock mechanism and the auxiliary lock structure to disengage from each other.

9. The clip applicator according to claim 8, wherein the clip-cartridge assembly comprises a clip-cartridge outer shell, the clip-cartridge outer shell comprises a clip-cartridge fixation shell and a clip-cartridge rotation shell that are rotatably connected with each other, an identification signal generation structure is arranged at a proximal end of the clip-cartridge fixation shell, an identification signal receiver is fixed in the adapter, and the identification signal receiver is in signal communication with the identification signal generation structure;

the adapter outer shell comprises a main body outer shell and a rotation outer shell, and the rotation outer shell is rotatably connected to the main body outer shell;

through cooperation of the lock mechanism and the lock structure, the clip-cartridge fixation shell and a guide ring are optionally locked, and the clip-cartridge rotation shell and the rotation shell are optionally locked;

the auxiliary lock mechanism cooperates with the auxiliary lock structure on the guide ring to lock the clip-cartridge fixation shell and the guide ring when the clip-cartridge assembly is plugged in place.

10. The clip applicator according to claim 9, wherein
the auxiliary lock mechanism comprises an elastic ring located in an inner wall groove of the clip-cartridge fixation shell, and one or at least two positioning protrusions connected to the elastic ring;
the auxiliary lock structure is one or at least two positioning holes arranged on an inner wall of the guide ring, and the positioning protrusion runs through a through hole on the clip-cartridge fixation shell to engage with the positioning hole.

11. The clip applicator according to claim 9, wherein
the lock structure comprises a lock groove arranged on an outer surface of the clip-cartridge fixation shell, and the lock groove is locked with a lock bead;
the lock structure further comprises a first plug member arranged on the clip-cartridge fixation shell, the first plug member is plugged into a first plug slot on the guide ring, and plug between the first plug member and the first plug slot provides a circumferential lock of the clip-cartridge fixation shell and the guide ring;
the lock structure further comprises a second plug member arranged on the clip-cartridge rotation shell, the second plug member is plugged into a second plug slot on the rotation outer shell, and plug between the second plug member and the second plug slot provides a circumferential lock of the clip-cartridge rotation shell and the rotation outer shell;
an axial distance between the plug member on the clip-cartridge fixation shell and the plug member on the clip-cartridge rotation shell is greater than an axial distance between the first plug slot on the guide ring and the second plug slot on the rotation outer shell.

12. The clip applicator according to claim 11, wherein
the identification signal generation structure is an identification information storage chip, the identification information storage chip is provided with two groups of pin needles that are in signal communication with the identification signal receiver, and when the first plug member is plugged into the first plug slot or the second plug member is plugged into the second plug slot, the identification signal receiver is connected with at least one group of pin needles;
each group of pin needles comprises one or at least two pin needles.

* * * * *